United States Patent [19]

Yuki et al.

[11] Patent Number: 5,371,196

[45] Date of Patent: Dec. 6, 1994

[54] PROCESS FOR PRODUCING SECRETORY IMMUNOGLOBULIN A PREPARATIONS

[75] Inventors: Yoshikazu Yuki; Motoko Baba; Mitsuo Shimizu; Kazuo Kato, all of Kobe; Hajime Hiratani, Sennan, all of Japan

[73] Assignee: JCR Pharmaceuticals Co., Ltd., Hyogo, Japan

[21] Appl. No.: 115,458

[22] Filed: Sep. 1, 1993

Related U.S. Application Data

[63] Continuation of Ser. No. 771,131, Oct. 3, 1991, abandoned.

[30] Foreign Application Priority Data

Oct. 5, 1990 [JP] Japan ........................ 2-269200

[51] Int. Cl.$^5$ ........................ A61L 2/18; A61K 35/14; A61K 35/16; C12N 7/06
[52] U.S. Cl. ................................ 530/390.1; 530/387.1; 530/382; 530/390.5; 530/388.1; 530/861
[58] Field of Search ............... 530/387.1, 390.1, 390.5

[56] References Cited

U.S. PATENT DOCUMENTS

| | | | |
|---|---|---|---|
| 3,415,804 | 12/1968 | Polson | 530/382 |
| 4,124,576 | 11/1978 | Coval | 530/387 |
| 4,439,421 | 3/1984 | Hooper et al. | 530/387 |
| 4,721,777 | 1/1988 | Uemura et al. | 530/387 |

FOREIGN PATENT DOCUMENTS

| | | |
|---|---|---|
| 0131740 | 1/1985 | European Pat. Off. |
| 0196761 | 2/1986 | European Pat. Off. |
| 0225581 | 10/1986 | European Pat. Off. |
| 0378208 | 1/1990 | European Pat. Off. |

OTHER PUBLICATIONS

Labib et al, J. Biol Chem. vol. 251:7, pp. 1969–1974, 1976 Bovine Secretory Component.

*Primary Examiner*—Howard E. Schain
*Assistant Examiner*—Plynn Touzeau
*Attorney, Agent, or Firm*—Burgess, Ryan and Wayne

[57] ABSTRACT

Secretory immunoglobulin A preparations substantially not containing virus are produced by a process wherein secretory immunoglobulin A which might be contaminated with viruses is (1) heated about 60° C. for about 10 hours, or (2) subjected to the reaction with tri-n-butyl phosphate and a surfactant and the heating as mentioned above, as liquidized form in an aqueous medium, and then polymerized matters are precipitated from the resulting solution by adding polyethyleneglycol thereto.

10 Claims, No Drawings

PROCESS FOR PRODUCING SECRETORY IMMUNOGLOBULIN A PREPARATIONS

This application is a continuation of application Ser. No. 771,131, filed Oct. 3, 1991, now abandoned.

FIELD OF THE INVENTION

This invention relates to a process for producing secretory immunoglobulin A (hereinafter abbreviated as sIgA) and a preparation substantially not containing denatured sIgA can be obtained by this invention.

BACKGROUND OF THE INVENTION

Secretory immunoglobulin A is an immunoglobulin contained in secretion from exocrine gland, particularly in a large amount in foremilk and it has protective function against bacteria and viruses on mucosa surface.

It is known that sIgA is effective in the cases for which supplementary local immunotherapy on mucosa can be applied as referred below; Primary immunodeficiency syndrome and diarrhea difficult to treat and aphthous stomatitis accompanied by secondary immunodeficiency (immunodeficiency by infection, nutritional disorders, drugs, etc.) (S. Matsumoto et al., Birth Defects 18, 229, 1983; Okino et al., Nihon Shonigakkai Shi, 84, 158, 1990):

Furthermore, it may be highly effective in treating recurrent upper respiratory inflammation (eg. otitis media) and treatment after operation of biliary obstruction (Kurono et al., Therapeutic Research 10, 4433, 1989).

It can not be denied that there is fear for the mixing of viruses such as hepatitis virus, AIDS virus cytomegalovirus, etc. into sIgA purified from foremilk. Accordingly, the inactivation of these viruses is indispensable on processing the sIgA to preparations thereof. However, there is no known process wherein the inactivation of the viruses are combined with the processes for purifying sIgA from foremilk.

With regard to the inactivation of viruses, heating process in the form of a liquid (hereinafter abbreviated as "heating as liquidized form") has been applied to serum protein such as albumin etc. as the most reliable process for inactivating viruses which might be mixed therein, according to a report of Murray (The New York Academy of Medicine, 31, 341, 1955). This process has been widely employed for a long time.

However, this process can be applied to only a heat-resistant material such as albumin, while most of protein are easily denatured by heat and liable to cause the decrease or disappearance of activity. Furthermore, this is not a process which can completely inactivate virus as far as hepatitis B virus is concerned.

On the other hand, Prince, Horowitz and Brotman (The Lancet March, 29, 206, 1986) disclosed that envelope containing viruses such as hepatitis B virus, AIDS virus, Non-A, Non-B Hepatitis Virus, etc. can be completely inactivated by treating at 24° to 30° C. for 6 hours in the presence of tri-n-butyl phosphate and a surfactant, and this process can be applied to many drugs originated from serum protein. However, this process seems to be ineffective to a group of viruses not having envelopes such as hepatitis A virus, etc.

SUMMARY OF THE INVENTION

The present invention intends to provide a process for producing sIgA preparations substantially not containing infectious viruses, substantially not containing denatured sIgA, and having high safety.

Present inventors carried out researches along the above purpose, and, as the result, found that sIgA preparations having high safety and effectiveness is obtained by combining "heating as liquidized form" and fractionation with polyethyleneglycol (hereinafter abbreviated as PEG) and further found that sIgA preparations having higher safety are obtained by combining the treatment with tri-n-butyl phosphate and a surfactant with "heating as liquidized form" and PEG-fractionation.

Present invention is (I) a process for producing a secretory immunoglobulin A preparation substantially not containing virus characterized in that secretory immunoglobulin A which might be contaminated with viruses is, as liquidized form in an aqueous medium, (1) heated at about 60° C. for about 10 hours, or (2) subjected to the treatment of reacting with tri-n-butyl phosphate and a surfactant, and the heat-treatment as mentioned above, and the resulting polymers are removed by the addition of polyethyleneglycol; and (II) a process for producing a secretory immunoglobulin A preparation substantially not containing virus characterized in that secretory immunoglobulin A which might be contaminated with viruses is reacted with tri-n-butyl phosphate and a surfactant as liquidized form in an aqueous medium, heated at about 60° C. for about 10 hours, and polymerized matters formed in the resulting aqueous solution of said globulin A is removed by adding polyethyleneglycol thereto.

In present invention, the starting material sIgA which might be contaminated with viruses is not limited particularly. It may be a sIgA fraction obtained from the milk of human or cattle, or a fraction of monoclonal antibody in sIgA type obtained from human or cattle, and it may be a fraction containing sIgA obtained from the foremilk of human or cattle, for example, a fraction containing sIgA obtained in each step of the following processes.

DETAILED DESCRIPTION OF THE INVENTION

(I) Centrifuging Process

The foremilk of human or cattle is centrifuged (e.g. 3,500 to 8,000 rpm., for 30 to 60 minutes), and then fat deposited as the upper layer or precipitates is removed. After filtration, the filtrate is adjusted to pH 4.2 to 4.6 and stirred at room temperature for 30 to 60 minutes, followed by removing precipitated casein by centrifugation.

(II) Process of Salting Out and Dialyzing

The solution thus obtained is neutralized and subjected to salting out with ammonium sulfate (saturated to 50 %). The precipitated sIgA fraction is recovered by centrifuging, and dissolved in 0.01 M phosphate buffer solution (pH 6.5 to 7.5), followed by dialyzation employing same buffer solution.

(III) Process of Treating with Anion Exchanger

The salted out fraction of sIgA is sufficiently dialyzed and then charged on a column of anion exchanger, preferably DEAE-Toyopearl® 650C or DEAE-Sephacel®, previously buffered with 0.01 M phosphate buffer solution (pH 6.5 to 7.5). The charging amount of the salted out sIgA fraction on the column is preferably 1 to 5 g as sIgA per 1 L of gel (filler) and the concentration of the protein is preferably 3 to 10 mg/ml. After washing the column with 5-fold column volume of the above buffer solution, sIgA is eluted from the column with 0.1 M phosphate buffer solution (pH 8.5 to 7.5) or a buffer solution prepared by adding 0.10 to 0.15 M of sodium chloride to 0.01 M phosphate buffer solution (pH 6.5 to 7.5).

(IV) Process of Treating with Heparinoid-immobilizing Column

A column immobilizing heparinoid such as heparin-Sepharose ®, heparin-Toyopearl ® or heparin-Sulfate Cellulofine ® is previously buffered with 0.1 M phosphate buffer solution (pH 6.5 to 7.5) or a buffer solution prepared by adding 0.1 to 0.15 M of sodium chloride to 0.01 M phosphate buffer solution (pH 6.5 to 7.5), and the above sIgA fraction eluted from the anion exchanger is charged on the buffered column. The charging amount of the sIgA fraction is preferably 10 to 50 g as sIgA per 1 L of gel (filler) and the concentration of the protein is preferably 3 to 10 mg/ml.

By collecting fractions passed through the column without being adsorbed, sIgA fraction free of lactoferrin can be obtained. As the resin employed in this process, preferably employed in industry is Sulfate Cellulofin ® not immobilizing high molecular substances thereon. This resin can be regenerated with 0.6 to 1.0 M sodium chloride.

(V) Process of Precipitation with Polyethyleneglycol

By adding PEG #4000 so as to make its concentration 20% w/v to the sIgA fraction subjected to the treating with the heparin-immobilizing column, sIgA fraction is precipitated. The precipitates are collected by centrifuging, dissolved in physiological saline to make about 20 mg/ml of sIgA solution.

As the starting material of present preparations, any of the sIgA fractions obtained in the above "(II) Process of salting out and dialyzing" and the consecutive processes may be employed. However, in the case of employing the fraction obtained in "(II) Process of salting out" or "(III) Process of treating with anion exchanger" for carrying out the process of present invention, it is preferable to perform the above process (III) or (IV) and the consecutive processes, after the present process.

In present invention, viruses are inactivated by heating as liquidized form in an aqueous medium at about 60° C. for about 10 hours.

SIgA can be dispersed in an aqueous solution of salts such as physiological saline and phosphate buffer solution to form a solution-like state and the heating is carried out in this state.

By heating at about 60° C. for about 10 hours, a considerable amount of sIgA is denatured, although sIgA still remains in the solution. However, it was found that the denaturation can be suppressed by the addition of a stabilizer (Ref. to Experiment 1).

As the stabilizer, there may be used sugar alcohols such as sorbitol, disaccharides such as cane sugar, and amino acids such as glycine. One or more of these stabilizers may be used. When one kind of the stabilizer is used, preferable is a sugar alcohol such as sorbitol. A disaccharide and an amino acid are preferably used jointly with each other.

After the heat-treatment, the solution contains polymerized sIgA dissolved therein, however, sIgA polymer and monomer can be separated from each other, because the polymer precipitates by adding PEG to the solution to make PEG concentration 5 to 10%, preferably 7 to 8%, whereas sIgA monomer begins to precipitate from 10% of PEG concentration, and most of the monomer precipitates at 15% and almost completely precipitates at 20 to 25% of PEG.

As PEG, there may be exemplified PEG #4000 (average molecular weight; 3,000), PEG #2000 (average molecular weight; 2,000), PEG #6000 (average molecular weight; 7,500), etc. Preferable pH in the fractionation with PEG is 6 to 8.

By the above heat-treatment, most of viruses are inactivated, however, when contamination with a heat-resistant virus such as hepatitis B virus, etc. is considered, it is desirable to carry out the treatment by reacting with tri-n-butyl phosphate and a surfactant.

Accordingly, the possibility of combining the above heat-treatment with the treatment with tri-n-butyl phosphate and a surfactant was investigated. As the result, it was found that the combination itself is possible, however, sIgA is polymerized and coagulated to some extent even in the treatment with tri-n-butyl phosphate and a surfactant. Therefore, in order to remove efficiently the coagulated polymer, it is convenient to carry out the heat-treating after the treatment with tri-n-butyl phosphate and a surfactant and then fractionation by PEG.

In the treatment with tri-n-butyl phosphate and a surfactant, the examples of the surfactant include nonionic surfactants such as Tween 80 and anionic surfactants such as sodium cholate. As to the concentration of tri-n-butyl phosphate and a surfactant in the treatment, the former may be 0.2 to 0.4% and the latter may be any concentration as far as it is not more than 1%. These agents may be reacted generally at 20° to 30° C. for 5 to 7 hours.

In an embodiment, 0.3% of tri-n-butyl phosphate and of Tween 80, or 0.3% of tri-n-butyl phosphate and 0.2% of sodium cholate are added as respective final concentrations to a solution containing sIgA, and the mixed solutions are treated at 24° C. and 30° C. for 6 hours, respectively.

Tri-n-butyl phosphate and the surfactant in the sIgA solution which has been subjected to the above treatment can be by adding PEG to the solution so as to make PEG concentration 20 to 25% causing sIgA to precipitate, and then centrifuging. The resultant sIgA precipitates are dissolved by adding a medium such as physiological saline thereto, and the solution is heated at about 60° C. for about 10 hours, preferably under the addition of stabilizer(s) mentioned above. Consecutively, the solution is subjected to the above PEG fractionation, thereby sIgA treated by the two steps of virus-inactivation is obtained.

In other embodiment, sIgA was precipitated from a sIgA solution which had been subjected to the first step of virus inactivation, by adding PEG to the concentration of 20% thereto, and tri-n-butyl phosphate and the surfactant were removed from the precipitates by centrifuging. The resultant sIgA was dissolved by adding physiological saline thereto so as to make 1% w/v solution (pH 7). As stabilizers, 50% w/v sorbitol-2 M glycine were added to the solution, and the mixture was subjected to the above "heating as liquidized form" (60° C. for 10 hours) and the fractionation with 8–23% PEG.

Respective yields in the embodiments were 63 and 60%, which were lower to some extent than that of treating by heating alone.

The neutralizing antibody potency of the sIgA prepared by this invention is as follows:

(1) Process of "Heating as Liquidized Form"—PEG Fractionation

SIgA prepared by the above process of "heating as liquidized form" and PEG fractionation, and sIgA prepared from same material by a process omitting the heat-treatment process from the above process were tested by direct agglutination employing *Escherichia coli* (NHI/J strain etc.) and the neutralizing antibody potency of these sIgAs to viruses such as rotavirus, echovirus, etc. were determined. By comparing the results obtained with both sIgAs, no difference was found between them in the direct agglutination with *Escherichia coli* as well as in the neutralizing antibody potency to the viruses, so that it was confirmed that the activity of sIgA is not impaired by this process (Ref. to Test Examples 1 and 2).

(2) Process of tri-n-butyl phosphate - surfactant - "heating as liquidized form" - PEG fractionation The direct agglutination employing *Escherichia coli* (NHI/J strain etc.) and the neutralizing antibody potency of sIgA prepared by this process was compared with those of sIgA prepared from same material by a process omitting the above steps. As the results, no large difference was observed between them in the direct agglutination of *Escherichia coli* as well as in the neutralizing antibody potency of viruses, so that the usefulness of present invention was found as in the above (1) (Ref. to Test Examples 3 and 4).

From the above results, it was also found that sIgA preparations prepared by present invention do not contain denatured sIgA.

Furthermore, according to a model experiment about the inactivation of viruses, it was clarified in high possibility that citomegalovirus and hepatitis A virus which are heat-resistant to the same extent as poliovirus as well as AIDS virus which is weaker in heat-resistance than the above viruses are inactivated by present heat-treating, and also even viruses which are highly heat-resistant such as hepatitis B or non-A non-B virus are inactivated by employing the treatment with tri-n-butyl phosphate and a surfactant jointly with the heat-treating (Ref. to Test Example 2).

The sIgA solution obtained by present invention may be dialyzed to physiological saline, etc. and then sterilized by membrane filtration, etc. The resulting solution may be administered as it is, or freeze-dried and processed to capsules to administer as an oral preparation. The form of the preparation varies according to the usage. In processing to the preparations, enteric coating may be applied, although this coating in not required particularly, because sIgA is a chemically and enzymatically stable substance. Present sIgA is employed as an agent for supplementary local immunotherapy on mucosa, hence oral administration and instillation in nose or eyes are considered in the administration, and intravenous injection is not necessarily meaningful, however, the mode of administration is not limited particularly.

Present invention is explained further by exemplifying Experiments, Examples and Test Examples in the following:

Experiment 1

Tests of Heat-stabilizing Agent and PEG Fractionation for sIgA

Experiments of heating a solution containing sIgA at 60° C. for 10 hours as a liquidized form in the presence or absence of heat-stabilizers were carried out, and the degree of polymerization-coagulation of sIgA was analyzed to screen best stabilizer as well as to investigate the optimal PEG concentration for removing the polymerized matters.

Generally, the heat-denature of protein is accompanied by a phenomenon that the protein is coagulated by polymerization and come to insolubilyze in water, and the reaction proceeds unreversibly. It is important in knowing the denature of protein to grasp the degree of polymerization-coagulation. Accordingly, in the first place, the solution of the above sIgA in 1% w/v physiological saline was treated as it is or under the addition of a stabilizer mentioned below at 60° C. for 10 hours. And then, the recovered amount of sIgA was analyzed by employing Superose ® 8 (produced by Pharmacia Co.) column. The results are shown in Table 1.

TABLE 1

Provisional experiment of heat-treating sIgA solution "as liquidized form"

| Stabilizer | Appearance after heat-treating | Recovery ratio of sIgA |
|---|---|---|
| (1) not added | whitely turbid | 19% |
| (2) 2M glycine | slightly, whitely turbid | 66% |
| (3) 50 w/v % sucrose | almost clear | 68% |
| (4) 50 w/v % sorbitol | almost clear | 77% |
| (5) 50 w/v % sucrose- 2M glycine | almost clear | 78% |
| (6) 50 w/v % sorbitol- 2M glycine | almost clear | 80% |

The sIgA samples obtained in Table 1 was diluted, PEG was added thereto to a concentration of 5 to 10%, preferably 7 to 8%, and the mixture was allowed to stand at 4° C. for 1 hour and then centrifuged. The amount of polymerized matters in the supernatant was investigated. As the result, it was found that most of the polymerized matters precipitates at the above PEG concentration in any of the cases. In order to know the yield of sIgA after removing sIgA polymer, PEG was further added to the supernatant of each sample containing 8% of PEG to make the final concentration 23%, whereby sIgA was completely precipitated and recovered. As the result, the recovery ratio of sIgA was 10% in the case that no stabilizer was added thereto, whereas respective yields of sIgA were 88, 87 and 73% in the cases that sorbitol, sucrose-glycine and sorbitol-glycine were added thereto as stabilizers, showing larger recovery ratios than in the above case.

SIgA monomer fraction begins to precipitate from 10% of PEG concentration, the most part of the monomer precipitates at 15% and almost completely precipitates at 20 to 30%.

From these results, it was found that, in the case of adding no stabilizer, the coagulation and precipitation of sIgA is observed making the solution turbid whirely by heating as liquidized form at 60° C. for 10 hours, however it is considerably suppressed by the addition of stabilizers.

Experiment 2

Test of Virus Activity after Treating of Inactivation

In Experiment 1, it was confirmed that the denature of sIgA in heat-treatment at 60° C. for 10 hours in the form of aqueous solution is suppressed by the presence of a stabilizer. However, this fact suggests a possibility that virus is not completely inactivated because there is a possibility that the protein constructing virus particles is also not denatured.

Accordingly, in order to prove that the treatment according to present invention is effective only to inactivate viruses, there were carried out experiments of virus inactivation by "heating as liquidized form" in the presence and absence of 50% w/v sorbitol - 2 M glycine as stabilizer, employing poliovirus (type 1) and vesicular stomatitis virus (VSV). Furthermore, since it is considered that protein itself may possibly be a stabilizer for virus, there was carried out experiments of "heating as liquidized form" in the presence of 2% or 50% w/v sorbitol - 2 M glycine to 60° C. for 10 hours, employing human albumin as a model protein. The results are shown in Table 2.

TABLE 2

| Virus inactivation by "heating as liquidized form" | | | |
|---|---|---|---|
| Virus | Stabilizer | Heat-treated "as liquidized form" at 60° C. for 10 hours | Not treated |
| Poliovirus | None | <3.1 | $5.6 \times 10^4$ |
|  | Presence | <3.1 | $5.6 \times 10^4$ |
|  | HSA/Stabilizer | <3.1 | $10.0 \times 10^4$ |
| VSV | None | <3.1 | $10.0 \times 10^4$ |
|  | Presence | <3.1 | $17.8 \times 10^4$ |
|  | HSA/Stabilizer | <3.1 | $31.6 \times 10^4$ |

(In the Table, numerals are $TCID_{50}$)

The results in Table 2 suggested high possibility that AIDS virus which is less heat-resistant than poliovirus, and cytomegalovirus and hepatitis A virus which are heat-resistant to same extent as poliovirus are inactivated. From the facts that any of poliovirus and VSV are inactivated by this treatment, it is considered that the inactivation has no relation to whether a virus has an envelope or not. However, it is not necessarily assured that hepatitis A and non-A non-B viruses which are highly heat-resistant can be inactivated only by this treatment.

Accordingly, there were carried out virus-inactivation experiments by treating with tri-n-butyl phosphate-surfactant which is considered effective against a virus having envelope such as hepatitis B or non-A non-B virus, or the like. Employing VSV having an envelope and poliovirus not having an envelope as viruses to be tested, virus-inactivation experiments were carried out, wherein respective viruses were treated at 24° C. and 30° C. for 6 hours under the addition of 0.3% tri-n-butyl phosphate -1% Tween, a surfactant, or 0.3% tri-n-butyl phosphate–0.2% sodium cholate. In consideration of the possibility that protein itself may be a stabilizer for viruses, experiments of treating by the above treatment under adding 2% of human albumin (HSA) as a model protein to the above agents were carried out simultaneously. The results are shown in Table 3.

TABLE 3

| Inactivation of viruses by treatment with tri-n-butyl phosphate (TNBP) - surfactant | | | | | |
|---|---|---|---|---|---|
|  |  | TNBP/Tween 80 | | TNBP/sodium cholate | |
| Virus | HSA | Treated | Not treated | Treated | not treated |
| Poliovirus | Non | $5.6 \times 10^5$ | $3.2 \times 10^5$ | $5.6 \times 10^4$ | $1.8 \times 10^4$ |
|  | Presence | $3.2 \times 10^4$ | $5.6 \times 10^4$ | $3.2 \times 10^4$ | $5.6 \times 10^4$ |
| VSV | Non | 31 | $3.2 \times 10^5$ | 31 | $5.6 \times 10^5$ |
|  | Presence | 31 | $1.8 \times 10^6$ | 31 | $1.0 \times 10^5$ |

(In the Table, numerals are $TCID_{50}$)

The results in Table 3 show that the treatment with tri-n-butyl phosphate - surfactant inactivates only a virus having an envelope and completely ineffective against a virus not having an envelope. Namely, it is considered that hepatitis B or non-A non-B virus, AIDS virus, etc. are inactivated, and hepatitis A virus, etc. can not be inactivated.

From these results, it is apparent that "heating as liquidized form" can inactivate most of pathogenic viruses, however more complete inactivation is required to a virus such as hepatitis B virus which can not be inactivated by "heating as liquidized form" at 60° C. for 10 hours, and hence it is desirable to perform the heat-treating together with treating with tri-n-butyl phosphate-surfactant.

EXAMPLE 1

After removing fat from 2 L of human foremilk by centrifugation, the supernatant was adjusted to pH 4.5 and Casein was removed therefrom by centrifugation. The supernatant thus obtained was salted out by adding ammonium sulfate thereto to 50% saturation. The resulting precipitates were collected and sufficiently dialyzed with 0.01 M phosphate buffer (pH 7.4). The dialyzate remained inside of the membrane was charged on 1L of the column of DEAm-Sephacel ® (produced by Pharmacia Co.) previously sufficiently buffered with the same buffer as above. After the column was sufficiently washed with the same buffer, sIgA was eluted therefrom with 0.01M phosphate buffer solution - 0.1 M sodium chloride, pH 7.4 (PBS). Consecutively, the eluate was charged on 100 ml of the column of heparin-Shephrose ® (produced by Pharmacia Co.) buffered sufficiently with PBS, and the unadsorbed portion was collected. By adding polyethylene glycol (PEG) #4000 (produced by Wako Pure Chemical, Ltd.) to the portion, sIgA was precipitated, the precipitates were collected and dissolved by adding physiological saline (produced by Otsuka Pharmaceutical Co., Ltd.) thereto to prepare 2% sIgA solution. To per ml of the solution, 0.5 g of sorbitol (produced by Wako Pure Chemical, Ltd.) was added to dissolve therein, and the resulting solution was poured dividedly into hard glass bottles and sealed. These bottles were sunk into hot water of 60° C. and heated for 10 hours. After the heating, the solution was diluted to 5-fold with physiological saline, PEG #4000 was added thereto so as to make its concentration 8% w/v, the mixed solution was allowed to stand at 4° C. for 2 hours, and the resulting precipitates were removed by centrifugation. To the solution thus obtained, PEG #4000 was added so as to make its final concentration 23% and the solution was allowed to stand at 4° C. for 8 hours. The resulting precipitates were collected by centrifugation and dissolved by adding physiological saline to make 2% sIgA solution. This solution was dialyzed employing physiological saline and sterilized by membrane filtration. The yield of sIgA from the foremilk was 40% (Lot 1/T). Furthermore, the abovementioned precipitates at 20% of PEG, which had not been heated, were dissolved with physiological saline to make 2% sIgA solution. After dialyzing with physiological saline, the solution was sterilized by membrane filtration to make a preparation (Lot 1/N).

EXAMPLE 2

A sIgA preparation was prepared from human foremilk by the same manner as in Example 1. The yield of sIgA from the foremilk was 40% (Lot 2/T). Another preparation was also prepared by dissolving the precipitates which were obtained at 20% of PEG and had not been treated by heating into physiological saline to make 2% sIgA solution, dialyzing the solution with physiological saline and sterilizing by membrane filtration (Lot 2/N).

EXAMPLE 3

Human foremilk was subjected to the removal of fat and casein and then to dialysis in the same manner as in Example 1. The resulting solution was charged on 7 L column of DEAE-Toyopearl® (produced by Tohso Corp.) previously sufficiently buffered with 0.01 M phosphate buffer (pH 7), and then the column was washed sufficiently with the same buffer, followed by eluting sIgA with 0.1 M phosphate buffer (pH 7). Consecutively, the eluate was charged on 600 ml column of Sulfate-Cellulofine® (produced by Seikagaku Kogyo Co.) previously sufficiently buffered with 0.1 M phosphate buffer (pH 7), the unadsorbed portion was collected, and PEG #4000 was added thereto so as to make the concentration of PEG 20% w/v to precipitate sIgA. The resultant precipitates were collected and dissolved by adding physiological saline thereto to make 2% sIgA solution. To per ml of the solution, 0.5 g of sorbitol and 0.15 g of glycine were added and dissolved therein and the mixed solution was treated at 60° C. for 10 hours.

After the above "heating as liquidized form", the solution was diluted to 5-fold with physiological saline, PEG #4000 was added to the diluted solution so as to make 7% w/v of PEG concentration, the solution thus obtained was allowed to stand at 4° C. for 1 hour, and then the resultant precipitates were removed by centrifugation. To the resulting solution, PEG #4000 was added to make a final concentration 20%, the mixed solution was allowed to stand at 4° C. for 6 hours, and the resulting precipitates were collected by centrifuging and dissolved by adding physiological saline to make 2% sIgA solution. The solution thus obtained was dialyzed with physiological saline and sterilized by membrane filtration. The yield of sIgA was 48% (Lot 3/T). Another preparation was also prepared by dissolving the precipitates which were obtained at 20% PEG and had not been treated by heating into physiological saline to make 2% sIgA solution, dialyzing the solution with physiological saline and sterilizing by membrane filtration.

EXAMPLE 4

In the same manner as in Example 3, 2% sIgA solution was prepared by subjecting 10 L of human foremilk to the removal of fat and casein, dialysis, column chromatography with DEAE-Toyopearl® and Sulfate-Cellulofine®, collecting sIgA fraction, precipitating sIgA by the addition of PEG #4000 to the fraction to make 20% w/v of PEG concentration, collecting the resulting precipitates and dissolving the precipitates with physiological saline.

The sIgA solution thus prepared was divided to three aliquot portions. To one of the portions, tri-n-butyl phosphate was added so as to make 0.3% and Tween, a surfactant, 80 to make 1%. To one other portion, tri-n-butyl phosphate was added so as to make 0.3% and sodium cholate to make 0.2%.

After the former portion was treated at 24° C., and the latter at 30° C., for 6 hours respectively, PEG #4000 was added to the both portions so as to make 20% w/v to precipitate sIgA. The precipitates resulting from each of the both portions were collected and dissolved by adding physiological saline thereto to obtain both 2% sIgA solutions. To per ml of these solutions each, 0.5 g of sorbitol and 0.15 g of glycine were added and dissolved therein, and both of the mixed solutions were treated at 60° C. for 10 hours. Each of the solutions treated by "heating as liquidized form" as mentioned above were diluted with physiological saline to 5-fold solution, PEG #4000 was added thereto so as to make 7% v/w, and then allowed to stand at 4° C. for 1 hour, followed by removing resultant precipitates by centrifuging. To each of the solutions thus obtained, PEG #4000 was added so as to make final concentration 20% and allowed to stand at 4° C. for 8 hours, the resultant precipitates were collected by centrifuging and dissolved by adding physiological saline thereto to make 2% sIgA solution, and the solution was dialyzed with physiological saline, followed by sterilization by membrane filtration. The preparation obtained by employing a surfactant with Tween 80 in the virus inactivation was designated Lot 4/T, and another one obtained by employing sodium cholate was designated Lot 4/C.

One other portion remained of the 3-divided portions was dialyzed with physiological saline, sterilized by membrane filtration and designated as non-treated lot (Lot 4/N). The yields of sIgA from foremilk were 40% in Lot 4/N, 38% in Lot 4/N.

TEST EXAMPLE 1

There were prepared solutions each containing a 4 mg/ml of each lot of the sIgA preparations prepared in Examples 2 and 3, and each solution was mixed with $2 \times 10^7$ of *Escherichia coli* strain NIH/J or strain b/8M. The agglutination images at 3 minutes after the mixing were compared each other. As the results, all of Lots 1/T, 2/T and 3/T showed the same agglutination images as those shown with Lots 1/N, 2/N and 3/N. While, in the case of a preparation which was made separately by subjecting to "heating as liquidized form" under adding no stabilizer at all and not subjecting to PEG fractionation, nearly 90% of the sIgA was denatured, and hence the sIgA solution showed no agglutination image with the 2 strains of *Escherichia coli* similarly to the contrast consisting of physiological saline only.

TEST EXAMPLE 2

Each Lot of sIgA preparations prepared in Examples 1 and 2 was subjected to determining neutralizing antibody potency to human rotavirus, poliovirus I, coxsakie B3 or A16 virus and echovirus. The results are shown in Table 4.

In the results, the Lots 1/T, 2/T and 3/T of present sIgA preparation exhibited the same neutralizing antibody valencies to these viruses as Lots 1/N, 2/N and 3/N which were not treated by heat.

TABLE 4

| sIgA* preparation Lot No. | Neutralizing antibody potencies of sIgA preparations to each virus: Neutralizing antibody potency to virus** | | | | |
|---|---|---|---|---|---|
| | Rota | Polio I | Coxsakie B3 | Coxsakie A16 | Echo 6 |
| 1/N | 4 | 10 | 76 | 22 | 19 |
| 1/T | 5 | 10 | 56 | 27 | 19 |
| 2/N | 19 | 5 | 2 | 7 | 4 |
| 2/T | 19 | 4 | 2 | 7 | 6 |
| 3/N | 726 | 2 | 8 | 6 | 7 |
| 3/T | 670 | 2 | 8 | 7 | 7 |

*Each sIgA preparation was used as 5 mg/ml solution made by diluting the preparation with a serum-free culture.
**Neutralizing antibody potency was evaluated by maximum dilution rate necessary to neutralize 50% of 100TCID$_{50}$ in each virus.

TEST EXAMPLE 3

Each solution containing 4 mg/ml of each Lot of sIgA preparations prepared in Example 4 was prepared and mixed with $2 \times 10^7$/ml of *Escherichia coli* strain NIH/J or B/8M-1. After 3 minutes form the mixing, agglutination images were compared with each other. As the results, both Lots 4/T and 4/C exhibited the same agglutination images as non-treated Lot 4/N.

TEST EXAMPLE 4

Each Lot of preparations made in Example 4 was subjected to the determination of neutralizing antibody potency to human rotavirus, polio I virus, coxsakie B3 or A16 virus and echovirus. The results are shown in Table 5.

In the results, there was not observed large difference btween neutralizing antibody potencies of present sIgA preparation Lot 4/C and $/T and those of non-treated Lot 4/N.

TABLE 5

| sIgA* preparation Lot No. | Neutralizing antibody potencies of sIgA A preparations to each virus: Neutralizing antibody potency to virus** | | | | |
|---|---|---|---|---|---|
| | Rota | Polio I | Coxsakie B3 | Coxsakie A16 | Echo 6 |
| 4/C | 203 | 1 | 33 | 1 | 1 |
| 4/T | 241 | 1 | 40 | 1 | 1 |
| 4/N | 298 | 1 | 48 | 1 | 1 |

*Each sIgA preparation was used as 5 mg/ml solution made by diluting the preparation with a serum-free culture.
**Neutralizing antibody potency was evaluated by maximum dilution rate necessary to neutralize 50% of 100TCID$_{50}$ in each virus.

Method of the Determination

The determination of sIgA was carried out by a developed sandwich ELISA method wherein anti-secretory-component-antibody (produced by Igaku Seibutsugaku Kenkyusho Co., Ltd.) is employed as a solid phase and peroxydase-labeled purified anti-alpha-chain-antibody prepared by the method of Hashida S. et al. (J. Appl. Biochem. 6 56 (1984)) using anti-alpha-chain-antibody (produced by Bio-yeda; Daiichi Kagaku Yakuhin Co,) is employed.

Infection valence of virus and neutralizing antibody potency to virus were calculated observing CPE caused with virus on a microplate employing the established cell line of MA104 originated from the kidney of rhesus monkey as cells for growing virus (Virus Jikkengaku Souron, Chapter 13, 1973; published by Marujen Co.).

We claim:

1. A process for producing a substantially non-virus containing secretory immunoglobulin A preparation which comprises heating a secretory immunoglobulin A, suspected of being contaminated with a virus, in liquidized form in an aqueous medium to a temperature of about 60° C. for 10 hours alone or in combination with reaction with tri-n-butyl phosphate and a surfactant, adding polyethylene glycol to the resulting solution so as to make a mixture containing 5 to 10 w/v percent of polyethylene glycol, removing precipitated polymerized products from the resulting solution, further adding polyethylene glycol to the remained solution so as to make its concentration 15 to 25 w/v percent, and recovering precipitated secretory immunoglobulin A from the solution.

2. A process for producing a substantially non-virus containing secretory immunoglobulin A which comprises reacting a secretory immunoglobulin A, suspected of being contaminated with a virus with tri-n-butyl phosphate and a surfactant, in liquidized form in an aqueous medium, heating the resulting product at about 60° C. for about 10 hours, adding polyethylene glycol to the resulting solution so as to make a mixture containing 5 to 10 w/v percent of polyethylene glycol, removing precipitated polymerized products from the resulting solution, further adding polyethylene glycol from the resulting solution, further adding polyethylene glycol to the remained solution so as to make its concentration 15 to 25 w/v percent, and recovering precipitated secretory immunoglobulin A from the solution.

3. The process of claim 1, wherein the immunoglobulin A in liquidized form in the resulting solution after treatment by heat alone or in combination with reaction with tri-n-butyl phosphate and a surfactant contains 1 to 5 w/v percent of immunoglobulin A, the addition of polyethylene glycol to the resulting solution is carried out at a pH of 6 to 8 to form a mixture, said mixture being allowed to stand for not less than 1 hour at about 4° C., and precipitated polymerized products are removed by centrifugation.

4. The process of claim 1, wherein the secretory immunoglobulin A is originated from a human, cattle or mouse.

5. The process of claim 1, wherein the secretory immunoglobulin A is a polyclonal or monoclonal antibody.

6. The process of claim 1, wherein the tri-n-butyl phosphate is reacted in a concentration of 0.2 to 0.4 percent and the surfactant is present in a concentration of 0.2 to 1 percent, said reaction taking place at 20° to 30° C. for about 5 to 7 hours.

7. The process of claim 1, wherein the surfactant is selected from the group consisting of TWEEN 80 and sodium cholate.

8. The process of claim 1, wherein the molecular weight of the polyethylene glycol is from 1,000 to 9,000.

9. The process of claim 1, wherein the heating step is carried out in the presence of at least one stabilizing agent selected from the group consisting of a sugar alcohol, a disaccharide and an amino acid.

10. The process of claim 9, wherein the concentration of the stabilizing agent is 1 to 3 moles when using an amino acid and 20 to 60 w/v percent when using a sugar alcohol or disaccharide, in 1 to 5 w/v percent solution of said secretory immunoglobulin A.

* * * * *